(12) United States Patent
Beckmann et al.

(10) Patent No.: US 6,949,366 B2
(45) Date of Patent: *Sep. 27, 2005

(54) CYTOKINES THAT BIND THE CELL SURFACE RECEPTOR HEK

(75) Inventors: M. Patricia Beckmann, Poulsbo, WA (US); Douglas P. Cerretti, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/904,954

(22) Filed: Jul. 12, 2001

(65) Prior Publication Data

US 2002/0010325 A1 Jan. 24, 2002

Related U.S. Application Data

(63) Continuation-in-part of application No. 08/161,132, filed on Dec. 3, 1993, now abandoned, which is a continuation-in-part of application No. 08/114,426, filed on Aug. 30, 1993, now abandoned, which is a continuation-in-part of application No. 08/109,745, filed on Aug. 20, 1993, now abandoned.

(51) Int. Cl.$^7$ .................. C12N 15/19; C12N 15/63; C12N 5/10; C07K 14/52
(52) U.S. Cl. ................ 435/69.5; 435/320.1; 435/252.3; 435/254.11; 435/325; 435/471; 435/71.1; 435/71.2; 536/23.5; 530/351
(58) Field of Search .......................... 536/23.1, 23.5; 530/350, 351; 435/69.5, 71.1, 71.2, 471, 325, 320.1, 252.3, 254.11

(56) References Cited

U.S. PATENT DOCUMENTS

| 5,185,438 A |   | 2/1993 | Lemischka |          |
|-------------|---|--------|-----------|----------|
| 5,516,658 A | * | 5/1996 | Beckmann et al. | 435/69.5 |
| 5,599,669 A |   | 2/1997 | Dixit |          |
| 5,728,813 A |   | 3/1998 | Lyman et al. |     |

FOREIGN PATENT DOCUMENTS

| EP | 0 597 503 A2 | 5/1994 |
| WO | WO 93/00425 | 1/1993 |
| WO | WO 94/11384 | 5/1994 |

OTHER PUBLICATIONS

Mikayama et al. Proc. Natl. Acad. Sci. USA vol. 90, pp. 10056–10060, 1993.*
Voet et al. Biochemistry, John Wiley & Sons, Inc., pp. 126–128 & 228–239, 1990.*
Cerretti, D., et al., "Isolation of cDNAs that Encode Ligands to the Receptor Tyrosine Kinases Hek and Elk: Emergence of a Family of Proteins that are Ligands for the Eph Related Kinases (LERKS)", Abstract for American Assoc. for Cancer Research conference on Growth Factors, Development, and Cancer, held in Interlaken Switzerland, Mar. 5–11, 1994.

Boyd, A., et al. "Isolation and Characterization of a Novel Receptor–type Protein Tyrosine Kinase (hek) from a Human Pre–B Cell Line," *J. Biol. Chem.* 267(5): 3262–3267, 1992.
Wicks, I., et al., "Molecular Cloning of HEK, the gene encoding a receptor tyrosine kinase expressed by human lymphoid tumor cell lines," *Proc. Natl. Acad. Sci. USA* 89: 1611–1615, 1992.
Wicks, I., et al., "Molecular Charcterisation of HEK, a Novel Human Receptor Tyrosine Kinase," Thesis for degree of Doctor of Philosophy, University of Melbourne, submitted Apr. 1992.
Lhotak, V., et al., "Characterization of Elk, a Brain–Specific Receptor Tyrosine Kinase," *Mol. Cell. Biol.* 11: 2496–2502, 1991.
Letwin, K., et al., "Novel protein–tyrosine kinase cDNAs related to *fps/fes* and *eph* cloned using anti–phosphotyrosine antibody," *Oncogene* 3: 621–627, 1988.
Sajjadi, F., et al., "Identification of a New *eph*–Related Receptor Tyrosine Kinase Gene From Mouse and Chicken that is Developmentally Regulated and Encodes at Least Two Forms of the Receptor," *New Biol.* 3: 769–788, 1991.
Chan, J., and Watt, V., "*eek* and *erk*, new members of the *eph* subclass of receptor protein–tyrosine kinases," *Oncogene* 6: 1057–1061, 1991.
Lindberg, R., and Hunter, T., "cDNA Cloning and Characterization of *eck*, an Epithelial Cell Receptor Protein–Tyrosine Kinase in the *eph/elk* Family of Protein Kinases," *Mol. Cell. Biol.,* 10: 6316–6324, 1990.
Pasquale, E., "Identification of chicken embryo kinase 5, a developmentally regulated receptor–type tyrosine kinase of the Eph family,"*Cell Regulation* 2: 523–534, 1991.
Hirai, H., et al., "A Novel Putative Tyrosine Kinase Receptor Encoded by the *eph* Gene," *Science* 238: 1717–1720, 1987.
Byrn, R., et al., "Biological properties of a CD4 immunoadhesin," *Nature* 344: 667–670, 1990.
Ashkenazi, A., et al., "Protection against endotoxic shock by a tumor necrosis factor receptor immunoadhesin," *Proc. Natl. Acad. Sci. USA* 88: 10535–10539, 1991.
Holzman, L., et al., "A Novel Immediate–Early Response Gene of Endothelium Is Induced by Cytokines and Encodes a Secreted Protein," *Mol. Cell. Biol.* 10: 5830–5838, 1990.
Ferguson, M., and Williams, A., "Cell–Surface Anchoring of Proteins via Glycosyl–Phosphatidylinositol Structures," *Ann. Rev. Biochem.* 57: 285–320, 1988.

(Continued)

*Primary Examiner*—Prema Mertz
(74) *Attorney, Agent, or Firm*—Finnegan, Henderson, Farabow, Garrett & Dunner, LLP

(57) ABSTRACT

Hek ligand (hek-L) polypeptides as well as DNA sequences, vectors and transformed host cells useful in providing hek-L polypeptides. The hek-L polypeptides bind to a cell surface receptor (hek) that is a member of the receptor tyrosine kinase family. Hek is expressed on cells that include certain tumor cell lines. The hek-L polypeptides also bind a distinct receptor tyrosine kinase known elk.

12 Claims, No Drawings

OTHER PUBLICATIONS

Böhme et al., "PCR mediated detection of a new human receptor–tyrosine–kinase, HEK 2," *Oncogene* 8: 2857–2862, 1993.

Bowie, J., et al., "Deciphering the Message in Protein Sequences: Tolerance to AminoAcid Substitutions," *Science* 247: 1306–1310, 1990.

Lerner, R., "Tapping the immunological repertoire to produce antibodies of predetermined specificity," *Nature* 299(14): 592–596, 1982.

Harlow, E. and Lane, D., "Antibodies a Laboratory Manual," Cold Spring Harbor Laboratory: Chapter 5, p. 76, 1988.

Letter to the Editor, Unified Nomenclature for Eph Family Receptors and Their Ligands, the Ephrins, Cell, 90: 403–404 (1997).

Cowan, et al, Ephrins In reverse, park and drive, Trends in Cell Biology, 12: 339–346 (2002).

* cited by examiner

CYTOKINES THAT BIND THE CELL SURFACE RECEPTOR HEK

CROSS-REFERENCE TO RELATED APPLICATIONS

This application is a continuation-in part of application Ser. No. 08/161,132, filed Dec. 3, 1993, now abandoned, which is a continuation-in part of application Ser. No. 08/114,426, filed Aug. 30, 1993, now abandoned, which is a continuation-in part of application Ser. No. 08/109,746, filed Aug. 20, 1993, now abandoned.

BACKGROUND OF THE INVENTION

Proteins known as the receptor tyrosine kinases have an intrinsic kinase activity that is activated upon ligand binding. This class of proteins is characterized by conserved structural motifs within the catalytic domains (Hanks et al., *Science*, 242:42, 1988) and can be subdivided into families based on structural features of the regions 5' to the catalytic domain.

Boyd et al. (*J. Biol. Chem.*, 267:3262, 1992) purified a cell surface glycoprotein exhibiting tyrosine kinase activity. The N-terminal amino acid sequence identified this protein as a member of the eph/elk family, and the protein was thus designated hek (human eph/elk-like kinase). A monoclonal antibody immunoreactive with hek was used to study hek expression on a number of human cell types (Boyd et al., supra). Hek antigen was detected on the human pre-B cell leukemia cell line LK63 (the cell line employed as the immunogen against which the antibody was raised) and the human T-cell leukemia cell line JM. The Raji B lymphoma cell line showed weak hek antigen expression, and the remaining cell lines tested (both normal and tumor cell lines, among which were hemopoietic cell lines that included pre-B and T-cell lines) were consistently negative. Of the normal and tumor tissue biopsy specimens that were also tested for hek antigen expression, none of the normal tissues was positive and only a very low proportion of hemopoietic tumors was positive.

Expression of hek transcripts on the above-described LK63 and JM cell lines, as well as on the human T-cell leukemia cell line HSB-2, has been demonstrated by northern blot analysis (Wicks et al., *Proc. Natl. Acad. Sci. USA*, 89:1611, 1992). Nucleotide and amino acid sequences for an isolated hek cDNA clone are presented in Wicks et al., supra.

The hek protein is very closely related to a number of other receptor tyrosine kinases, including elk (Letwin et al., *Oncogene* 3:621, 1988 and Lhotak et al., *Mol. Cell. Biol.* 11:2496, 1991); the hek homologs mek4 and cek4 (Sajjadi et al. *New Biol.* 3:769, 1991); eek (Chan et al. *Oncogene* 6:1057, 1991); erk (Chan et al. supra.), eck (Lindberg et al. *Mol. Cell. Biol.* 10:6316, 1990); cek5 (Pasquale, E. B. *Cell Regulation* 2:523, 1991); and eph (Hirai et al. *Science* 238:1717, 1987). The proteins of this subfamily are related not only in their cytoplasmic domains, but also in their extracellular domains, which are 41 to 68% identical. Interestingly, the tissue distributions of these various receptors are diverse. For example, expression of elk mRNA has been reported to be limited to testis and brain (Lhotak et al., supra), whereas eck is found not only in these same two tissues but in lung, intestine, kidney, spleen, ovary, and skin as well.

Ligands for the receptor tyrosine kinases are a diverse group of proteins that affect the growth, differentiation, and survival of cells expressing the receptors. To date, no ligand for hek has been discovered. Identification of the putative ligand or ligands that bind hek would prove useful in investigating the nature of cellular processes regulated by the hek protein.

SUMMARY OF THE INVENTION

The present invention provides novel cytokines designated hek ligands (hek-L) that bind to the cell surface receptor known as hek. The present invention also provides isolated DNA encoding the hek-L proteins, expression vectors comprising the isolated DNA, and a method for producing hek-L by cultivating host cells containing the expression vectors under conditions appropriate for expression of the hek-L protein. Antibodies directed against hek-L proteins or an immunogenic fragment thereof are also disclosed.

DETAILED DESCRIPTION OF THE INVENTION cDNAs encoding novel protein ligands that bind to the cell surface protein known as hek have been isolated in accordance with the present invention. Also provided are expression vectors comprising the hek ligand (hek-L) cDNA and methods for producing recombinant hek-L polypeptides by cultivating host cells containing the expression vectors under conditions appropriate for expression of hek-L, and recovering the expressed hek-L. Purified hek-L protein is also encompassed by the present invention, including soluble forms of the protein.

The present invention also provides hek-L or antigenic fragments thereof that can act as immunogens to generate antibodies specific to the hek-L immunogens. Monoclonal antibodies specific for hek-L or antigenic fragments thereof thus can be prepared.

The novel cytokines disclosed herein are ligands for hek, a cell surface receptor that is a member of the receptor tyrosine kinase family. One use of the hek ligands of the present invention is as research tools for studying the role that hek-L, in conjunction with hek, may play in growth or differentiation of cells bearing the hek receptor. Biological signals that may be initiated by binding of a hek-L to hek on a cell can be investigated. The possibility that hek plays a role in tumorigenesis has been suggested (Boyd et al., supra). The hek ligands provided herein are useful for studying what effect binding of hek-L to the cognate receptor may have on tumorigenesis.

The hek-L polypeptides of the present invention also may be employed in in vitro assays for detection of hek or hek-L or the interactions thereof. Since hek antigen has been detected on certain leukemic cell lines, hek-L may be employed as a carrier to deliver diagnostic or cytotoxic agents to such cells. These and other uses of hek ligands are further discussed below.

The hek-L proteins of the present invention also have been found to bind to the receptor tyrosine kinase known as elk. Elk has been described by Letwin et al., *Oncogene* 3:621, 1988 and Lhotak et al., *Mol. Cell. Biol.* 11:2496, 1991. Scatchard analysis revealed a biphasic pattern of elk binding for both hek-L proteins, as described in Example 5. Thus, the hek-L proteins disclosed herein also may be employed to bind elk, e.g., in various assay procedures. However, the elk ligand (elk-L) protein described in Example 5 generally would be preferred for such uses in view of the higher affinity of elk-L for elk.

The binding studies described in Example 5 also revealed that elk ligand (elk-L) binds hek (biphasic binding pattern).

A related protein known as B61 (Holzman et al., *Mol. Cell. Biol.* 10:5830, 1990) was found to bind both hek (linear pattern) and elk (biphasic pattern). The relative affinities are shown in Tables I and II of Example 5.

To identify cells suitable for use as nucleic acid sources in the attempt to clone hek-L DNA, different types of cells were screened for the ability to bind hek (in the form of a fusion protein comprising human hek and an antibody Fc polypeptide). A human T-cell leukemia cell line was positive for hek/Fc binding, and a cDNA expression library was derived therefrom. Two distinct cDNA clones encoding human hek-L were successfully isolated by screening clones for expression of a hek/Fc-binding protein, as described in Example 3. The DNA sequence and encoded amino acid sequence of one human hek-L cDNA clone are set forth in SEQ ID NO:1 and SEQ ID NO:2. DNA and encoded amino acid sequences of a second human hek-L clone are presented in SEQ ID NO:3 and SEQ ID NO:4. Comparison of both the nucleotide and encoded amino acid sequences of the human hek-L cDNA clones with the Genbank and Swisspro databases showed that the sequences of the hek ligands were unique. The amino acid sequences of the hek-binding proteins encoded by the two clones are 38% identical.

Human hek-L cDNA was isolated from the first positive clone and inserted into the Bam HI site (in the multiple cloning site region) of cloning vector pBLUESCRIPT® SK(−), available from Stratagene Cloning Systems, La Jolla, Calif. The resulting recombinant vector, designated A2/pBS, in *E. coli* DH5α cells, was deposited with the American Type Culture Collection on Aug. 11, 1993, and assigned accession no. ATCC 69384. Human hek-L cDNA was isolated from the second positive clone and inserted into the Bam HI site of pBLUESCRIPT® SK(−). The resulting recombinant vector, designated C6/pBS, in *E. coli* DH5α cells, was deposited with the American Type Culture Collection on Aug. 25, 1993, and assigned accession no. ATCC 69395. Both deposits were made under the terms of the Budapest Treaty.

The hek-L of SEQ ID NO:2 (encoded by the cDNA of clone A2) comprises an N-terminal signal peptide (amino acids −19 through −1), an extracellular domain (amino acids 1 through 202), and a C-terminal hydrophobic region that begins with amino acid 203. The hek-L of SEQ ID NO:4 (encoded by the cDNA of clone C6) comprises an N-terminal signal peptide (amino acids −22 through −1), an extracellular domain (amino acids 1 through 160), and a C-terminal hydrophobic region that begins with amino acid 161.

The hek-L proteins expressed by clones A2 and C6 were found to be anchored to the cell surface via glycosyl-phosphatidylinositol (GPI) linkage. GPI membrane anchors, including the chemical structure and processing thereof, are described in Ferguson, M. and A. Williams, *Ann. Rev. Biochem.*, 57:285, 1988 (hereby incorporated by reference). When initially expressed, certain proteins comprise a C-terminal hydrophobic domain that contains signals for GPI anchoring. A cleavage site is located upstream, often about 10–12 amino acids upstream of the N-terminus of the hydrophobic domain. Post-translational processing includes cleavage of the protein at this cleavage site. A GPI anchor attaches to the newly exposed C-terminal amino acid of the processed, mature protein. Thus, when the hek-L proteins are expressed in cells that recognize the GPI anchoring signals in the hydrophobic domain, the full length amino acid sequences of SEQ ID NOS:2 and 4 represent precursor forms of the proteins.

Based on consensus sequences derived from other GPI-anchored proteins, likely cleavage sites in the hek-L proteins of the present invention are between amino acids 194 and 195 of SEQ ID NO:2 and between amino acids 148 and 149 of SEQ ID NO:4. After cleavage of the protein, a GPI moiety attaches to the serine residue that is now the C-terminus of the processed protein (amino acid 194 of SEQ ID NO:2 and amino acid 148 of SEQ ID NO:4). It is possible that cleavage occurs elsewhere upstream of the hydrophobic region in the hek-L proteins.

The term "hek-L" as used herein refers to a genus of polypeptides which are capable of binding hek and exhibit homology (preferably being at least 80% homologous) to the hek-L protein of SEQ ID NO:2 or SEQ ID NO:4. Human hek-L is within the scope of the present invention, as are hek-L proteins derived from other mammalian species including but not limited to murine, rat, bovine, porcine, or various primate species. As used herein, the term "hek-L" includes both membrane-bound and soluble (secreted) forms of the protein. Truncated proteins that retain the hek-binding property are encompassed by the present invention. Such truncated proteins include, for example, soluble hek-L comprising only the extracellular (receptor binding) domain but lacking the hydrophobic domain.

The human hek-L cDNA may be radiolabeled and used as a probe to isolate other mammalian hek-L cDNAs by cross-species hybridization. For example, a cDNA library prepared from T-cell leukemic cell lines of other mammalian species may be screened with radiolabeled human hek-L cDNA to isolate a positive clone. Alternatively, mRNAs isolated from various cell lines can be screened by Northern hybridization to determine a suitable source of mammalian hek-L mRNA for use in cloning a hek-L gene.

Although a hek/Fc fusion protein was employed in the screening procedures described in Examples 2 and 3 below, hek can be used to screen clones and candidate cell lines for expression of hek-L proteins. The hek/Fc fusion protein, however, offers the advantage of being easily purified. In addition, disulfide bonds form between the Fc regions of two separate fusion protein chains, creating dimers.

Other antibody Fc regions may be substituted for the human IgG1 Fc region mutein described in Example 1. Other suitable Fc regions are those that can bind with high affinity to protein A or protein G, and include the Fc region of murine IgG1 or fragments of the human IgG1 Fc region, e.g., fragments comprising at least the hinge region so that interchain disulfide bonds will form.

One embodiment of the present invention provides soluble hek-L polypeptides. Soluble hek-L polypeptides comprise all or part of the extracellular domain of a native hek-L but lack the hydrophobic region that contains signals that would cause retention of the polypeptide on a cell membrane. Soluble hek-L polypeptides advantageously comprise the native (or a heterologous) signal peptide when initially synthesized to promote secretion, but the signal peptide is cleaved upon secretion of hek-L from the cell. The soluble hek-L polypeptides that may be employed retain the ability to bind the hek receptor. Soluble hek-L may also include part of the hydrophobic region provided that the soluble hek-L protein is capable of being secreted.

Soluble hek-L may be identified (and distinguished from its non-soluble membrane-bound counterparts) by separating intact cells which express the desired protein from the culture medium, e.g., by centrifugation, and assaying the medium (supernatant) for the presence of the desired protein. The presence of hek-L in the medium indicates that the protein was secreted from the cells and thus is a soluble form of the desired protein. Soluble hek-L may be a naturally-occurring form of this protein, e.g., arising from alternative splicing. Further, GPI-linked hek-L may be released or shed from the cell surface into the culture medium, e.g., by the action of a protease or other enzyme.

The use of soluble forms of hek-L is advantageous for certain applications. Purification of the proteins from recombinant host cells is facilitated, since the soluble proteins are secreted from the cells. Further, soluble proteins are generally more suitable for intravenous administration.

Examples of soluble hek-L polypeptides include those comprising the entire extracellular domain of a native hek-L protein. One such soluble hek-L protein comprises amino acids 1 through 202 of SEQ ID NO:2, and another comprises amino acids 1 through 160 of SEQ ID NO:4. When initially expressed within a host cell, the soluble protein may additionally comprise one of the heterologous signal peptides described below that is functional within the host cells employed. Alternatively, the protein may initially comprise the native signal peptide, such that the hek-L comprises amino acids −19 through 202 of SEQ ID NO:2 or amino acids −22 through 160 of SEQ ID NO:4. Soluble hek-L proteins may be truncated to delete the C-terminus up to and including the amino acid that serves as a GPI attachment site. Examples include proteins comprising amino acids 1–193 of SEQ ID NO:2 or amino acids 1-147 of SEQ ID NO:4, as discussed above. Although the GPI attachment site may be deleted, deletion of the hydrophobic domain is believed to be sufficient to prevent GPI anchoring of the protein to the cell membrane. In further embodiments, the proteins may be truncated at the C-terminus so that the C-terminal amino acid is any amino acid between amino acids 193 and 202 of SEQ ID NO:2, or between amino acids 147 and 160 of SEQ ID NO:4. DNA sequences encoding soluble hek-L proteins are encompassed by the present invention.

Truncated hek-L, including soluble polypeptides, may be prepared by any of a number of conventional techniques. A desired DNA sequence may be chemically synthesized using known techniques. DNA fragments also may be produced by restriction endonuclease digestion of a full length cloned DNA sequence, and isolated by electrophoresis on agarose gels. Oligonucleotides that reconstruct the 5' or 3'-terminus of a DNA fragment to a desired point may be synthesized. The oligonucleotide may contain a restriction endonuclease cleavage site upstream of the desired coding sequence and position an initiation codon (ATG) at the 5' end of the coding sequence. The well known polymerase chain reaction procedure also may be employed to isolate a DNA sequence encoding a desired protein fragment. As a further alternative, known mutagenesis techniques may be employed to insert a stop codon at a desired point, e.g., immediately downstream of the codon for the last amino acid of the extracellular domain.

Certain embodiments of the present invention provide isolated DNA comprising a nucleotide sequence selected from the group consisting of nucleotides 83–796 (entire coding region), 83–745 (encoding the signal peptide and extracellular domain), 140–796 (encoding the protein without the signal peptide) and 140–745 (encoding the extracellular domain) of SEQ ID NO:1. Also provided is isolated DNA comprising a nucleotide sequence selected from the group consisting of nucleotides 28–630 (entire coding region), 28–573 (encoding the signal peptide and extracellular domain), 94–630 (encoding the protein without the signal peptide), and 94–573 (encoding the extracellular domain) of SEQ ID NO:3. DNAs encoding biologically active fragments of the proteins of SEQ ID NO:2 and SEQ ID NO:4 are also provided, including but not limited to DNA encoding the above-described hek-L proteins truncated at the C-terminus.

The hek-L DNA of the present invention includes cDNA, chemically synthesized DNA, DNA isolated by PCR, genomic DNA, and combinations thereof. Genomic hek-L DNA may be isolated by hybridization to the cDNA of clones A2 or C6, using standard techniques.

The present invention provides purified hek-L polypeptides, both recombinant and non-recombinant. Variants and derivatives of native hek-L proteins that retain the desired biological activity (e.g., the ability to bind hek) are also within the scope of the present invention. In one embodiment of the present invention, mature hek-L protein is characterized by the N-terminal amino acid sequence Leu-Leu-Ala-Gln-Gly-Pro-Gly-Gly-Ala-Leu-Gly-Asn. In another embodiment, mature hek-L protein is characterized by the N-terminal amino acid sequence Gly-Ser-Ser-Leu-Arg-His-Val-Val-Tyr-Trp-Asn-Ser.

hek-L variants may be obtained by mutations of nucleotide sequences coding for native hek-L polypeptides, for example. A hek-L variant, as referred to herein, is a polypeptide substantially homologous to a native hek-L, but which has an amino acid sequence different from that of a native hek-L (human, murine or other mammalian species) because of one or more deletions, insertions or substitutions. Such variants that bind hek are equivalents of the native hek-binding proteins having the amino acid sequences presented in SEQ ID NO:2 and SEQ ID NO:4.

Variant DNA and amino acid sequences of the present invention preferably are at least 80% identical, most preferably at least 90% identical, to a native hek-L sequence such as the native sequences of SEQ ID NOS:1–4. For fragments, the percent identity is calculated for that portion of a native sequence that is present in the fragment. Certain embodiments of the present invention provide hek-L polypeptides comprising an amino acid sequence that is at least 80% identical to a sequence selected from the group consisting of amino acids 1–194, 1–202 and 1≧219 of SEQ ID NO:2 and amino acids 1–148, 1–160, and 1–179 of SEQ ID NO:4.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, which are incorporated by reference herein.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

hek-L also may be modified to create hek-L derivatives by forming covalent or aggregative conjugates with other chemical moieties, such as glycosyl groups, lipids, phosphate, acetyl groups and the like. Covalent derivatives of hek-L may be prepared by linking the chemical moieties to functional groups on hek-L amino acid side chains or at the N-terminus or C-terminus of a hek-L polypeptide or the extracellular domain thereof. Other derivatives of hek-L within the scope of this invention include covalent or aggregative conjugates of hek-L or its fragments with other proteins or polypeptides, such as by synthesis in recombinant culture as N-terminal or C-terminal fusions.

hek ligand when initially expressed in a recombinant system may comprise a signal or leader sequence (native or heterologous) at the N-terminus of a hek-L polypeptide. The signal or leader peptide co-translationally or post-translationally directs transfer of the protein from its site of synthesis to a site outside of the cell membrane or cell wall, and is cleaved from the mature protein during the secretion process. Examples of suitable heterologous signal peptides, which are generally chosen according to the expression system to be employed, are described below. hek-L polypeptide fusions can comprise peptides added to facilitate purification and identification of hek-L. Such peptides include, for example, poly-His or the antigenic identification peptides described in U.S. Pat. No. 5,011,912 and in Hopp et al., Bio/Technology 6:1204, 1988. One such peptide is the FLAG® peptide, Asp-Tyr-Lys-Asp-Asp-Asp-Asp-Lys (DYKDDDDK), which is highly antigenic and provides an epitope reversibly bound by a specific monoclonal antibody, enabling rapid assay and facile purification of expressed recombinant protein. Fusion proteins capped with this peptide may also be resistant to intracellular degradation in E. coli. A murine hybridoma designated 4E11 produces a monoclonal antibody that binds the peptide DYKDDDDK in the presence of certain divalent metal cations (as described in U.S. Pat. No. 5,011,912, hereby incorporated by reference) and has been deposited with the American Type Culture Collection under accession no. HB 9259.

The present invention further includes hek-L polypeptides with or without associated native-pattern glycosylation. hek-L expressed in yeast or mammalian expression systems (e.g., COS-7 cells) may be similar to or significantly different from a native hek-L polypeptide in molecular weight and glycosylation pattern, depending upon the choice of expression system. Expression of hek-L polypeptides in bacterial expression systems, such as E. coli, provides non-glycosylated molecules.

DNA constructs that encode various additions or substitutions of amino acid residues or sequences, or deletions of terminal or internal residues or sequences not needed for biological activity or binding can be prepared. For example, N-glycosylation sites in the hek-L extracellular domain can be modified to preclude glycosylation, allowing expression of a more homogeneous, reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

Three N-glycosylation sites are found in the hek-L encoded by clone A2, at amino acids 19–21, 48–50, and 81–83 of SEQ ID NO:2. One N-glycosylation site is found in the hek-L encoded by clone C6, at amino acids 11–13 of SEQ ID NO:4.

In another example, sequences encoding Cys residues that are not essential for biological activity can be altered to cause the Cys residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. KEX2 protease processing sites are found in the hek-L of SEQ ID NO:2 at amino acids 26–27, 87–88, and 199–200. The hek-L of SEQ ID NO:4 comprises KEX2 protease processing sites at amino acids 73–74 and 134–135.

Naturally occurring hek-L variants are also encompassed by the present invention. Examples of such variants are proteins that result from alternative mRNA splicing events or from proteolytic cleavage of the hek-L protein, wherein the hek-binding property is retained. Alternative splicing of mRNA may yield a truncated but biologically active hek-L protein, such as a naturally occurring soluble form of the protein, for example. Variations attributable to proteolysis include, for example, differences in the N- or C-termini upon expression in different types of host cells, due to proteolytic removal of one or more terminal amino acids from the hek-L protein (generally from 1–5 terminal amino acids). Signal peptides may be cleaved at different positions in a given protein, resulting in variations of the N-terminal amino acid of the mature protein.

In one expression system, the N-terminal amino acid of a hek-L protein encoded by clone C6 was amino acid 4 (Leu) of SEQ ID NO:4. One preparation of a soluble hek-L/Fc fusion protein derived from clone A2 comprised a mixture of fusion proteins having amino acid 12 (Asn) of SEQ ID NO:2 as the N-terminal amino acid (about 60%) and fusion proteins in which amino acid 1 (Leu) of SEQ ID NO:2 was the N-terminal amino acid. Certain embodiments of the present invention thus are directed to proteins (soluble or membrane-bound) in which the N-terminal amino acid is any of amino acids 1–4 of SEQ ID NO:4, or any of amino acids 1–12 of SEQ ID NO:2.

Due to the known degeneracy of the genetic code wherein more than one codon can encode the same amino acid, a DNA sequence may vary from that presented in SEQ ID NOS:1 or 3, and still encode a hek-L protein having the amino acid sequence of SEQ ID NOS:2 or 4. Such variant DNA sequences may result from silent mutations (e.g., occurring during PCR amplification), and may be the product of deliberate mutagenesis of a native sequence.

The present invention thus provides isolated DNA sequences encoding biologically active hek-L, selected from: (a) DNA derived from the coding region of a native mammalian hek-L gene (e.g., cDNA comprising the coding region of the nucleotide sequence presented in SEQ ID NO: 1 or SEQ ID NO:3); and (b) DNA which is degenerate as a result of the genetic code to a DNA defined in (a) and which encodes biologically active hek-L. The hek-L proteins encoded by such DNA sequences are encompassed by the present invention.

The hek-L DNA of the present invention includes cDNA, chemically synthesized DNA, DNA isolated by PCR, genomic DNA, and combinations thereof. Genomic hek-L DNA may be isolated by hybridization to the cDNA of clones A2 or C6, using standard techniques.

Assays for Biological Activity

Variants possessing the ability to bind hek may be identified by any suitable assay. Conventional assay techniques also are useful for analyzing the hek-binding activity of a native hek-L protein. Biological activity of hek-L may be determined, for example, by competition for binding to the ligand binding domain of hek (i.e. competitive binding assays).

One type of a competitive binding assay for hek-L polypeptide uses a radiolabeled, soluble human hek-L and intact cells expressing cell surface hek. Instead of intact cells, one could substitute soluble hek (such as a hek/Fc fusion protein) bound to a solid phase through a Protein A or Protein G interaction with the Fc region of the fusion protein. Another type of competitive binding assay utilizes radiolabeled soluble hek such as a hek/Fc fusion protein, and intact cells expressing hek-L. Alternatively, soluble hek-L could be bound to a solid phase.

Competitive binding assays can be performed using standard methodology. For example, radiolabeled hek-L can be used to compete with a putative hek-L homolog to assay for binding activity against surface-bound hek. Qualitative results can be obtained by competitive autoradiographic plate binding assays, or Scatchard plots may be utilized to generate quantitative results.

Alternatively, soluble hek can be bound to a solid phase such as a column chromatography matrix or a similar substrate suitable for analysis for the presence of a detectable moiety such as $^{125}$I-labeled hek-L. Binding to a solid phase can be accomplished, for example, by binding a hek/Fc fusion protein to a protein A or protein G-containing matrix.

The binding characteristics of hek-L (including variants) may also be determined using labeled, soluble hek (for example, $^{125}$I-hek/Fc) in competition assays similar to those described above. In this case, however, intact cells expressing hek-L, or soluble hek-L bound to a solid substrate, are used to measure the extent to which a sample containing a putative hek variant competes for binding of a labeled soluble hek to hek-L.

A preferred assay for detecting hek-binding activity of a membrane-bound hek-L is as follows. A modified indirect binding assay was devised, using the hek/Fc fusion protein prepared in Example 1 and the $^{125}$I-labeled mouse anti-human IgG Fc antibody described in Example 3 to avoid direct radiolabeling of hek/Fc. Cells expressing endogenous hek-L (e.g., the CCRF-HSB-2 cell line described in Example 2) are exposed to varying concentrations of hek/Fc, followed by a constant saturating concentration of the $^{125}$I-antibody as follows.

CCRF-HSB-2 cells are cultivated in suspension culture in 96-well culture plates. The cells ($2 \times 10^6$ cells/well) are incubated in the presence or absence of various concentrations of hek/Fc in binding medium (RPMI 1640 medium, 1% bovine serum albumin, 0.2% sodium azide and 20 mM Hepes, pH 7.2) for one hour at 37° C. Cells are then washed once with PBS and incubated with $^{125}$I-mouse and-human IgG Fc (40 ng/ml) in binding medium with gentle agitation for one hour at 37° C. Cells and unbound $^{125}$I-antibody are separated by the pthalate oil separation method, essentially as described by Dower et al., *J. Immunol.* 132:751 (1984).

An assay for hek/Fc-binding to cells expressing recombinant membrane-bound hek-L may be conducted as described in Example 5. An indirect binding assay was employed.

A preferred assay for analyzing the hek-binding activity of soluble hek-L is as follows. The assay detects the ability of a soluble hek-L to inhibit binding of a hek/Fc fusion protein to the CCRF-HSB-2 cell line that expresses endogenous hek-L, as described in Example 2.

Conditioned supernatant (culture medium) from CV-1/EBNA cells transfected with an expression vector expressing a soluble hek-L is titrated in a 96-well plate. A constant amount of hek/Fc (1 µg/well) is added to each well, followed by $1-2 \times 10^6$ CCRF-HSB-2 cells per well, in binding medium. The plate is incubated at 37° C. for one hour. Cells are washed twice with PBS, then pelleted by centrifugation. 125I-mouse anti-human IgG Fc is added to each well at a constant concentration, and the plate is incubated for an additional hour at 37° C. The $^{125}$I-mouse anti-human IgG Fc binds to the hek/Fc that bound to the CCRF-HSB-2 cells. After the final incubation, cells are harvested over phthalate oil-containing tubes to separate the bound and free $^{125}$I-mouse anti-human IgG Fc. The radioactivity is quantitated using a gamma counter.

Uses of hek-L

The hek-L of the present invention can be used in a binding assay to detect cells expressing hek. For example, hek-L or the extracellular domain or a fragment thereof can be conjugated to a detectable moiety such as $^{125}$I. Radiolabeling with $^{125}$I can be performed by any of several standard methodologies that yield a functional $^{125}$I-hek-L molecule labeled to high specific activity. Alternatively, another detectable moiety such as an enzyme that can catalyze a colorometric or fluorometric reaction, biotin or avidin may be used. Cells to be tested for hek expression can be contacted with labeled hek-L. After incubation, unbound labeled hek-L is removed and binding is measured using the detectable moiety.

The hek ligand proteins disclosed herein also may be employed to measure the biological activity of hek protein in terms of binding affinity for hek-L. To illustrate, hek-L may be employed in a binding affinity study to measure the biological activity of a hek protein that has been stored at different temperatures, or produced in different cell types. The biological activity of a hek protein thus can be ascertained before it is used in a research study, for example.

Hek-L proteins find use as reagents that may be employed by those conducting "quality assurance" studies, e.g., to monitor shelf life and stability of hek protein under different conditions. Hek ligands may be used in determining whether biological activity is retained after modification of a hek protein (e.g., chemical modification, truncation, mutation, etc.). The binding affinity of the modified hek protein for a hek-L is compared to that of an unmodified hek protein to detect any adverse impact of the modification on biological activity of hek.

A different use of a hek ligand is as a reagent in protein purification procedures. Hek-L or hek-L/Fc fusion proteins may be attached to a solid support material by conventional techniques and used to purify hek by affinity chromatography.

Hek-L polypeptides also find use as carriers for delivering agents attached thereto to cells bearing the hek cell surface antigen. Expression of hek antigen has been reported for certain leukemic cell lines, including the human T-cell leukemia cell lines designated JM and HSB-2 and the human pre-B cell leukemia cell line designated LK63 (Boyd et al., *J. Biol. Chem.* 267:3262, 1992, and Wicks et al., *Proc. Nat. Acad. Sci. USA*, 89:1611, 1992). Hek-L proteins thus can be used to deliver diagnostic or therapeutic agents to these cells (or to other cell types found to express hek on the cell surface) in in vitro or in vivo procedures.

One example of such use is to expose a hek+leukemic cell line to a therapeutic agent/hek-L conjugate to assess whether the agent exhibits cytotoxicity toward the leukemia cells. A number of different therapeutic agents attached to hek-L may be included in an assay to detect and compare the cytotoxic effect of the agents on the leukemia cells. Hek-L/ diagnostic agent conjugates may be employed to detect the presence of $hek^+$ cells in vitro or in vivo.

Diagnostic and therapeutic agents that may be attached to a hek-L polypeptide include, but are not limited to, drugs, toxins, radionuclides, chromophores, fluorescent compounds, enzymes that catalyze a colorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the hek-L by any suitable conventional procedure. Hek-L, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to hek-L by using a suitable bifunctional chelating agent, for example.

Conjugates comprising hek-L and a suitable diagnostic or therapeutic agent (preferably covalently linked) are thus prepared. The conjugates are administered or otherwise employed in an amount appropriate for the particular application.

As described in Example 5, the hek-L proteins provided herein also are capable of binding a receptor known as elk. Thus, hek-L has additional uses stemming from the elk-binding property, analogous to those uses described above that stemmed from the hek-binding property. Hek-L can be used to detect elk in various assays. An antibody that binds hek may be employed in an assay, if appropriate, to block binding of hek to hek-L while allowing binding of elk to hek-L. Hek ligands may be employed in assessing the biological activity of elk proteins in terms of the binding affinity of an elk protein or variant thereof for a hek-L. Hek-L proteins also find use in purifying elk proteins by affinity chromatography.

Hek-L Oligomers

The present invention encompasses hek-L polypeptides in the form of oligomers, such as dimers or trimers. Oligomers may be formed by disulfide bonds between cysteine residues on different hek-L polypeptides. In one embodiment of the invention, a hek-L dimer is created by fusing hek-L to the Fc region of an antibody (IgG1) in a manner that does not interfere with binding of hek-L to the hek ligand binding domain. The term "Fc polypeptide" includes native and mutein forms, as well as truncated Fc polypeptides containing the hinge region that promotes dimerization. The Fc polypeptide preferably is fused to the C-terminus of a soluble hek-L (comprising only the extracellular domain). Preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference.

A fusion of the hek-L to an Fc or Fc mutein polypeptide may be prepared by procedures analogous to those described in Example 1 for preparation of a hek/Fc mutein fusion. A gene fusion encoding the hek-L/Fc fusion protein is inserted into an appropriate expression vector and transfected into host cells. The expressed hek-L/Fc fusion proteins are allowed to assemble much like antibody molecules, whereupon interchain disulfide bonds form between Fc polypeptides, yielding divalent hek-L. Alternatively, the native Fc polypeptide from which the mutein was derived may be employed.

If fusion proteins are made with both heavy and light chains of an antibody, it is possible to form a hek-L oligomer with as many as four hek-L extracellular regions. Alternatively, one can link two soluble hek-L domains with a peptide linker such as those described in U.S. Pat. No. 5,073,627.

In particular embodiments of the present invention, hek-L DNA encoding amino acids −19 through 202 of SEQ ID NO:1 or amino acids −22 through 157 of SEQ ID NO:3 was fused to the 5' end of DNA encoding the Fc mutein described in Example 1, and inserted into the expression vector pDC410 (described in Example 3). CV1-EBNA-1 cells transfected with the resulting recombinant expression vector were cultivated to express the soluble hek-L/Fc fusion protein.

The present invention provides oligomers of hek-L extracellular domains or fragments thereof, linked by disulfide interactions, or expressed as fusion polymers with or without spacer amino acid linking groups. For example, a dimer of the hek-L extracellular domain can be linked by an IgG Fc region linking group.

Expression Systems

The present invention provides recombinant expression vectors for expression of hek-L, and host cells transformed with the expression vectors. Any suitable expression system may be employed. The vectors include a hek-L DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the hek-L DNA sequence. Thus, a promoter nucleotide sequence is operably linked to a hek-L DNA sequence if the promoter nucleotide sequence controls the transcription of the hek-L DNA sequence. The ability to replicate in the desired host cells, usually conferred by an origin of replication, and a selection gene by which transformants are identified, may additionally be incorporated into the expression vector.

In addition, sequences encoding appropriate signal peptides that are not native to the hek-L gene can be incorporated into expression vectors. For example, a DNA sequence for a signal peptide (secretory leader) may be fused in frame to the hek-L sequence so that the hek-L is initially translated as a fusion protein comprising the signal peptide. A signal peptide that is functional in the intended host cells enhances extracellular secretion of the hek-L polypeptide. The signal peptide is cleaved from the hek-L polypeptide upon secretion of hek-L from the cell.

Suitable host cells for expression of hek-L polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce hek-L polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a hek-L polypeptide may include an N-terminal methionine residue to facilitate expression of the recombinant polypeptide in the prokaryotic host cell. The N-terminal Met may be cleaved from the expressed recombinant hek-L polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a hek-L DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9 (ATCC 37092)) and pPLc28 (resident in *E. coli* RR1 (ATCC 53082)).

hek-L alternatively may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the hek-L polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant hek-L polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CV1 (ATCC CCL 70) as described by McMahan et al. (*EMBO J.* 10:2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the HindIII site toward the BglI site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses.

In place of DNA encoding the native signal sequence, the vector may contain DNA encoding a heterologous signal sequence. Examples include the signal sequence for interleukin-7 (IL-7) described in U.S. Pat. No. 4,965,195; the signal sequence for interleukin-2 receptor described in Cosman et al., *Nature* 312:768 (1984); the interleukin-4 signal peptide described in EP 367,566; the type I interleukin-1 receptor signal peptide described in U.S. Pat. No. 4,968,607; and the type II interleukin-1 receptor signal peptide described in EP 460,846.

Protein Purification

The present invention provides substantially homogeneous hek-L protein, which may be produced by recombinant expression systems as described above or purified from naturally occurring cells. The hek-L is purified to substantial homogeneity, as indicated by a single protein band upon analysis by SDS-polyacrylamide gel electrophoresis (SDS-PAGE).

One process for producing the hek-L protein comprises culturing a host cell transformed with an expression vector comprising a DNA sequence that encodes hek-L under conditions such that hek-L is expressed. The hek-L protein is then recovered from culture medium or cell extracts, depending upon the expression system employed. As the skilled artisan will recognize, procedures for purifying the recombinant hek-L will vary according to such factors as the type of host cells employed and whether or not the hek-L is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify hek-L. Some or all of the foregoing purification steps, in various combinations, can be employed to provide a substantially homogeneous recombinant protein.

It is also possible to utilize an affinity column comprising the ligand binding domain of hek to affinity-purify expressed hek-L polypeptides. hek-L polypeptides can be removed from an affinity column in a high salt elution buffer and then dialyzed into a lower salt buffer for use. Alternatively, the affinity column may comprise an antibody that binds hek-L. In a further alternative, an affinity column comprises a hek/Fc fusion protein bound to a Protein A column.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells may be employed to express hek-L as a secreted polypeptide. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

The present invention provides pharmaceutical compositions comprising a hek-L polypeptide and a physiologically acceptable carrier, diluent, or excipient. Such compositions may comprise buffers, antioxidants such as ascorbic acid, low molecular weight (less than about 10 residues) polypeptides, proteins, amino acids, carbohydrates including glucose, sucrose, or dextrins, chelating agents such as EDTA, glutathione and other stabilizers and excipients. Neutral buffered saline or saline mixed with conspecific serum albumin are exemplary appropriate diluents.

Nucleic Acid Fragments

The present invention further provides fragments of the hek-L nucleotide sequences presented herein. Such fragments desirably comprise at least about 14 nucleotides of the sequence presented in SEQ ID NOS:1 or 3. DNA and RNA complements of said fragments are provided herein, along with both single-stranded and double-stranded forms of the hek-L DNA.

Among the uses of such hek-L nucleic acid fragments is use as a probe. Such probes may be employed in cross-species hybridization procedures to isolate hek-L DNA from additional mammalian species. As one example, a probe corresponding to the extracellular domain of hek-L may be employed. The probes also find use in detecting the presence of hek-L nucleic acids in in vitro assays and in such procedures as Northern and Southern blots. Cell types expressing hek-L can be identified. Such procedures are well known, and the skilled artisan can choose a probe of suitable length, depending on the particular intended application.

Other useful fragments of the hek-L nucleic acids are antisense or sense oligonucleotides comprise a single-stranded nucleic acid sequence (either RNA or DNA) capable of binding to target hek-L mRNA (sense) or hek-L DNA (antisense) sequences. Antisense or sense oligonucleotides, according to the present invention, may comprise a fragment of the coding region of hek-L cDNA shown in SEQ ID NO:1 or SEQ ID NO:3, or the DNA or RNA complement thereof. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *Bio-Techniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of hek-L proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to illustrate particular embodiments and not to limit the scope of the invention.

EXAMPLE 1

Preparation of Soluble hek/Fc Fusion Protein

This example describes construction of an expression vector encoding a soluble hek/Fc fusion protein, for use in isolating cDNA clones encoding a hek ligand (hek-L). A DNA and encoded amino acid sequence for human hek cDNA is presented in Wicks et al. (*Proc. Nat'l. Acad. Sci. USA*, 89:1611, 1992), hereby incorporated by reference. This hek protein comprises (from N- to C-terminus) an extracellular domain, a transmembrane domain, and a cytoplasmic domain.

Two DNA fragments, one encoding an N-terminal fragment of the extracellular domain of hek and the other encoding a C-terminal fragment of the hek extracellular domain, were isolated by polymerase chain reactions (PCR) conducted under standard conditions, using oligonucleotide primers based on the hek nucleotide sequence published by Wicks et al., supra. The template for the PCR was cDNA prepared from mRNA isolated from a human T-cell leukemic cell line designated CCRF-HSB-2 (ATCC CCL-120.1). The PCR products containing the 5' end of the hek DNA were digested with SpeI and HindIII to isolate a DNA fragment extending from the 5' end of the mature human hek sequence (i.e., lacking DNA encoding the signal sequence) to a HindIII site found in the hek gene. The PCR products containing the 3' end of the hek extracellular domain DNA were digested with HindIII and ClaI to isolate a fragment extending from the internal HindIII site to a ClaI site just downstream of the 3' end of the sequence encoding the hek extracellular domain. The ClaI site is in a multiple cloning site (mcs) introduced just downstream of the extracellular domain.

DNA encoding a mutein of the Fc region of a human IgG1 antibody was isolated. This Fc mutein DNA and the polypeptide encoded thereby are described in U.S. patent application Ser. No. 08/097,827, entitled "Novel Cytokine Which is a Ligand for OX40" filed Jul. 23, 1993, which application is hereby incorporated by reference. The mutein DNA was derived from a native Fc polypeptide-encoding DNA by site-directed mutagenesis conducted essentially as described by Deng and Nickoloff, *Anal. Biochem.* 200:81 (1992). The amino acid sequence of the Fc mutein polypeptide is identical to that of the native Fc polypeptide described in PCT application WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

A recombinant vector containing the Fc mutein DNA was cleaved with ClaI and NotI, which cleave the vector in a polylinker region immediately upstream and downstream, respectively, of the Fc mutein DNA insert. The desired Fc mutein-encoding fragment was isolated.

The mutein Fc polypeptide extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate hek/Fc fusion proteins, creating dimers.

A mammalian expression vector designated SMAG4 was cleaved with SpeI and NotI. The SMAG4 vector comprises a murine interleukin-7 signal peptide-encoding sequence (described in U.S. Pat. No. 4,965,195) inserted into the mammalian high expression vector pDC201 (described in Sims et al., *Science* 241:585, 1988, and in PCT application WO 89/03884), which is also capable of replication in *E. coli*. SpeI cleaves the vector immediately downstream of the IL-7 signal peptide-encoding sequence. NotI cleaves approximately 155 bp downstream of the SpeI site in a multiple cloning site of the vector. The large SpeI/NotI fragment containing the vector sequences and the IL-7 signal peptide-encoding DNA was isolated.

A four-way ligation was conducted to insert the two hek-encoding DNA fragments and the Fc mutein-encoding DNA fragment described above into the SpeI/NotI cleaved SMAG4 expression vector. *E. coli* cells were transfected with the ligation mixture and the desired recombinant vector was isolated therefrom. The isolated vector encodes a fusion protein comprising (from N- to C-terminus) the murine IL-7 signal peptide, the hek extracellular domain, four amino acids encoded by the introduced mcs, and the Fc mutein.

The expression vector was then co-transfected with plasmid pSV3.NEO into CV1/EBNA cells. The CV1/EBNA cell line (ATCC CRL 10478) was derived from a monkey kidney cell line as described in McMahan et al. (*EMBO J.*, 10:2821, 1991). Vector pSV3.NEO expresses SV40 T-antigen, which is not produced by the host cells. The pSV3.NEO vector is similar to pSV3 (Mulligan and Berg, *Proc. Natl. Acad. Sci. USA* 78:2072, 1981), but additionally contains a neomycin resistance gene. The transformed cells were cultivated to allow transient expression of the fusion protein, which is secreted into the culture medium via the murine IL-7 signal peptide. The fusion protein was purified on a protein A Sepharose column, eluted, and used to screen cells for the ability to bind the hek/Fc protein, as described in Examples 2 and 3.

EXAMPLE 2

Screening Cells for hek/Fc Binding

Various cell types were screened for the ability to bind hek/Fc, to identify candidate cell types useful as nucleic acid sources in an attempt to clone a hek ligand. Cells were incubated with the hek/Fc protein prepared in Example 1, followed by a biotinylated mouse and-human Fc antibody, followed by streptavidin-phycoerythrin (Becton Dickinson). Cells were washed between steps to remove unbound reagents. The biotinylated antibody was purchased from Jackson Immunoresearch Laboratories, West Grove, Pa. This antibody showed minimal binding to Fc proteins bound to the Fcγ receptor. Streptavidin binds to the biotin molecule attached to the anti-human Fc antibody, which in turn binds to the Fc portion of the hek/Fc fusion protein. Phycoerythrin is a fluorescent phycobiliprotein which serves as a detectable label. The level of fluorescence signal was measured for each cell type using a FACScan® flow cytometer (Becton Dickinson).

A human T-cell leukemia cell line designated CCRF-HSB-2 (ATCC CCL 120.1) was positive for hek/Fc binding. CCRF-HSB-2 cells were sorted four times by FACS (fluorescence-activated cell sorting) to derive cells expressing higher levels of hek/Fc-binding protein.

EXAMPLE 3

Isolation of Hek Ligand cDNA mRNA was isolated from the 4× sorted CCRF-HSB-2 cells and double-stranded cDNA was synthesized on the mRNA template by standard techniques. A cDNA library was prepared by ligating the cDNA into the BglII site of pDC410 by an adapter method similar to that described by Haymerle et al. (*Nucl. Acids Res.* 14:8615, 1986). pDC410 is an expression vector similar to pDC406 (McMahan et al., *EMBO J.*, 10:2821, 1991). In pDC410, the EBV origin of replication of pDC406 is replaced by DNA encoding the SV40 large T antigen (driven from an SV40 promoter). The pDC410 multiple cloning site (mcs) differs from that of pDC406 in that it contains additional restriction sites and three stop codons (one in each reading frame). A T7 polymerase promoter downstream of the mcs facilitates sequencing of DNA inserted into the mcs.

*E. coli* strain DH5α cells transfected with the cDNA library in pDC410 were plated to provide approximately 2000 colonies per plate. Colonies were scraped from each plate, pooled, and plasmid DNA prepared from each pool. The pooled DNA representing about 2000 colonies was then used to transfect a sub-confluent layer of CV1/EBNA-1 cells (described in Example 1). Prior to transfection, the CV1/EBNA-1 cells were maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and were plated at a density of $2 \times 10^5$ cells/well on single-well chambered slides (Lab-Tek). Transfection involved DEAE-dextran followed by chloroquine treatment, similar to the procedure described by Luthman et al., *Nucl. Acids Res.* 11:1295, 1983) and McCutchan et al., *J. Natl. Cancer Inst.* 41:351, 1986). Briefly, slides were pretreated with 1 ml human fibronectin (10 µg/ml in PBS) for 30 minutes followed by 1 wash with PBS. Media was removed from the adherent cell layer and replaced with 1.5 ml complete medium containing 66.6 µM chloroquine sulfate. 0.2 mls of DNA solution (2 µg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for 2.5 to 20 minutes followed by replacement of the solution with fresh complete medium. The cells were cultured for 2 to 3 days to permit transient expression of the inserted sequences.

Transfected monolayers of CV1/EBNA-1 cells were assayed for expression of hek-L by the slide autoradiography procedure of Gearing et al. (*EMBO J.* 8:3667, 1989), as follows. Mouse anti-human Fc antibody (Jackson Immunoresearch Laboratories, West Grove, Pa.) was radioiodinated by the chloramine-T method for use in the assay. Briefly, a P6 column was prepared according to the manufacturer's instructions. In a microfuge tube, 10 μg of antibody was dissolved in 10× of PBS. 2000 μCi of carrier-free Na$^{125}$I was added and the solution was mixed well. 15 μl of a freshly prepared solution of chloramine-T (32 μg/ml in 0.05 M sodium phosphate buffer (pH 7.2) was then added and the mixture was incubated for 30 minutes at room temperature. The mixture was immediately applied to the P6 column. The radiolabeled antibody was then eluted from the column by collecting 100–150 μl fractions of eluate. Binding media (RPMI 1640 containing 25 mg/ml bovine serum albumin, 2 mg/ml sodium azide, 20 mM Hepes pH 7.2) was added to peak fractions to bring the total volume of each fraction to 2 ml. Radioiodination yielded specific activities in the range of 5–10×10$^{15}$ cpm/mmol protein.

Slide autoradiography was conducted as follows. Transfected CV1/EBNA-1 cells (adhered to chambered slides) were washed once with binding medium with nonfat dry milk (BM-NFDM) (RPMI medium 1640 containing 25 mg/ml bovine serum albumin (BSA), 2 mg/ml sodium azide, 20 mM HEPES, pH 7.2, and 50 mg/ml nonfat dry milk). Cells were then incubated with hek/Fc (prepared in Example 1) in BM-NFDM (1 μg/ml) for 1 hour at room temperature. After incubation, the cell monolayers in the chambered slides were washed three times with BM-NFDM to remove unbound hek/Fc fusion protein and then incubated with 40 ng/ml $^{125}$I-mouse anti-human Fc antibody (a 1:50 dilution) for 1 hour at room temperature. The cells were washed three times with BM-NFDM, followed by 2 washes with phosphate-buffered saline (PBS) to remove unbound $^{125}$I-mouse anti-human Fc antibody. The cells were fixed by incubating for 30 minutes at room temperature in 2.5% glutaraldehyde in PBS, pH 7.3, washed twice in PBS and air dried. The chambered slides containing the cells were exposed on a Phophorimager (Molecular Dynamics) overnight, then dipped in Kodak GTNB-2 photographic emulsion (6× dilution in water) and exposed in the dark for 3–5 days at 4° C. in a light proof box. The slides were then developed for approximately 4 minutes in Kodak D 19 developer (40 g/500 ml water), rinsed in water and fixed in Agfa G433C fixer. The slides were individually examined with a microscope at 25–40× magnification and positive cells expressing hek-L were identified by the presence of autoradiographic silver grains against a light background.

Approximately 300,000 cDNAs were screened in pools of approximately 2,000 cDNAs to identify transfectant pools showing multiple cells positive for hek/Fc binding. A positive pool was then partitioned into pools of 500 and again screened by slide autoradiography. A positive pool was identified, partitioned into pools of 100, and screened by the same procedure. Individual colonies from a positive pool were screened until a single clone (clone #A2) that directed synthesis of a surface protein with detectable hek/Fc binding activity was identified. A second clone, designated C6, was isolated from a different positive pool. The cDNA inserts of both clones were sequenced.

The nucleotide and encoded amino acid sequences of the coding region of the human hek ligand cDNA of clone A2 are presented in SEQ ID NO:1 and SEQ ID NO:2. The protein comprises an N-terminal signal peptide (amino acids −19 to −1), an extracellular domain (amino acids 1–202) and a C-terminal domain containing a hydrophobic region (amino acids 203–219).

Human hek-L cDNA was excised from clone A2 by digestion with BglII. The excised cDNA was cloned into the BamHI site (in the multiple cloning site) of pBLUE-SCRIPT® SK(−) (Stratagene Cloning Systems, La Jolla, Calif.). The resulting vector (designated A2/pBS) in E. coli DH5α cells was deposited with the American Type Culture Collection, Rockville, Md., USA (ATCC) on Aug. 11, 1993, and assigned accession number ATCC 69384. The deposit was made under the terms of the Budapest Treaty.

The nucleotide and encoded amino acid sequences of the coding region of the human hek ligand cDNA of clone C6 are presented in SEQ ID NO:3 and SEQ ID NO:4. The protein comprises an N-terminal signal peptide (amino acids −22 to −1), an extracellular domain (amino acids 1–160), and a C-terminal domain containing a hydrophobic region (amino acids 161–179).

Human hek-L cDNA was excised from clone C6 by digestion with BglII and inserted into the BamHI site of pBLUESCRIPT® SK(−). The resulting vector (designated C6/pBS) in E. coli DH5α cells was deposited with the American Type Culture Collection, Rockville, Md., USA (ATCC) on Aug. 25, 1993 and assigned accession number ATCC 69395. The deposit was made under the terms of the Budapest Treaty.

The above-described boundaries of the domains of the hek-L proteins are approximate, as will be appreciated by the skilled artisan. For example, regarding the hek-L encoded by clone A2, the signal peptide most likely comprises amino acids −19 to −1, but it is possible that amino acids −19 through 3 constitute the signal peptide. Thus, cleavage of the signal peptide may occur between amino acids −1 and 1 or between amino acids 3 and 4, or at both positions. The terms "signal peptide" and "mature protein" as used herein in reference to the clone A2-encoded hek-L are understood to encompass both alternatives, as well as other alternatives described herein for hek-L polypeptides encoded by clone A2 or C6.

The hek-L proteins encoded by clones A2 and C6 have been found to be attached to the cell membrane via glycosylphosphatidylinositol (GPI) groups. The hydrophobic domains thus are believed to contain signals for GPI anchoring. Processing of proteins to effect GPI anchoring, which includes cleavage of C-terminal sequences, is described above.

EXAMPLE 4

Monoclonal Antibodies to hek-L

This example illustrates the preparation of monoclonal antibodies to hek-L. hek-L is expressed in mammalian host cells such as COS-7 or CV-1/EBNA-1 cells and purified using hek/Fc affinity chromatography. Purified hek-L (or a fragment thereof such as the extracellular domain or immunogenic peptide fragments thereof) can be used to generate monoclonal antibodies against hek-L using conventional techniques, for example, those techniques described in U.S. Pat. No. 4,411,993. Briefly, mice are immunized with hek-L as an immunogen emulsified in complete Freund's adjuvant, and injected in amounts ranging from 10–100 µg subcutaneously or intraperitoneally. Ten to twelve days later, the immunized animals are boosted with additional hek-L emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked Immunosorbent Assay), for hek-L antibodies.

Following detection of an appropriate antibody titer, positive animals are provided one last intravenous injection of hek-L in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified hek-L by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c mice to produce ascites containing high concentrations of anti-hek-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to hek-L.

EXAMPLE 5

Binding Studies

The affinity of the hek ligands of the present invention for hek was determined. The hek ligands were also found to bind to a receptor tyrosine kinase known as elk, which is distinct from hek. The ability of certain other proteins to bind to hek or elk was investigated as well. These studies were conducted as follows.

a) Hek Binding

CV1-EBNA-1 cells (described in example 1) in 12-well plates (2.5×10$^5$ cells/well) were transfected with clone A2 or C6 (clone A2 cDNA or clone C6 cDNA in expression vector pDC410, as described in Example 3). The transfected cells were cultured for two days to permit expression of the hek-L proteins, which were retained on the cell membrane. The cells then were washed with BM-NFDM (see Example 3) and incubated with various concentrations of the human hek/Fc fusion protein prepared in Example 1, for 1 hour at room temperature. Subsequently, cells were washed and incubated with the $^{125}$I-labeled mouse anti-human IgG antibody prepared in Example 3 (40 ng/ml) in binding medium with gentle agitation for 1 hour at 37° C. Cells then were harvested by trypsinization. In all assays, non-specific binding of $^{125}$I antibody was assayed in the absence of hek/Fc as well as in the presence of a 200-fold molar excess of unlabeled mouse anti-human IgG antibody. Free and cell-bound $^{125}$I-antibody were quantified on a Packard Autogamma Counter. Affinity calculations (Scatchard, *Ann.*

*N.Y. Acad. Sci.* 51:660, 1949) were generated on RS/1 (BBN Software, Boston, Mass.) run on a Microvax computer. CV1-EBNA-1 cells transfected with an "empty" pDC410 vector were included in the same binding study as a control.

Hek/Fc binding to CV1-EBNA-1 cells expressing two different recombinant proteins, human elk-L and human B61, also was analyzed in the above-described experiment. The cells were transfected with elk ligand (elk-L) or B61 cDNA in vector pDC410. The expressed proteins were cell membrane bound.

Elk-L binds to a receptor known as elk, which, like hek, is a member of the eph/elk family of receptor tyrosine kinases (see the "Background of the Invention" section above). Elk-L was included in this study to investigate whether or not it would bind to a different receptor of the same family (i.e., hek). The protein known as B61 has been identified as the product of a novel immediate-early response gene induced by TNF in human umbilical vein endothelial cells (Holzman et al., *Mol. Cell. Biol.* 10:5830, 1990). B61 was included in the study because of its degree of homology to elk-L (33% identity at the amino acid level).

The nucleotide sequence of isolated B61 cDNA and the amino acid sequence encoded thereby are presented in Holzman et al., supra, hereby incorporated by reference in its entirety. Methods for producing and recovering B61 are also described. along with certain structural characteristics and properties of the protein. Nucleotide and encoded amino acid sequences for elk-L cDNA are described in copending U.S. application Ser. No. 07/977,693, filed Nov. 13, 1992, and hereby incorporated by reference in its entirety. Production and purification of elk-L are also described, and certain functional domains of the protein are identified. *E. coli* DH5α cells transformed with human elk-L cDNA inserted into the SmaI site (in the mcs) of cloning vector pBLUESCRIPT®SK (Stratagene, La Jolla, Calif.) was deposited as ATCC 69085 on Oct. 9, 1992.

The results of the study were as follows:

TABLE I

| | Binding affinity for hek/Fc ($K_a$) |
|---|---|
| pDC410 | — |
| B61 | 5.5 × 10$^7$ M$^{-1}$ |
| elk-L | 2.3 × 10$^7$ M$^{-1}$; 2.9 × 10$^6$ M$^{-1}$ |
| hek-L A2 | 2.0 × 10$^8$ M$^{-1}$ |
| hek-L C6 | 2.0 × 10$^8$ M$^{-1}$ |

The empty vector exhibited no detectable hek/Fc binding. B61 bound hek/Fc with relatively moderate affinity, exhibiting a single affinity class of binding. The binding of hek/Fc to elk-L resulted in a biphasic pattern, indicating two lower-affinity binding components (affinity constants 2.3×10$^7$ M$^{-1}$ and 2.9×10$^6$ M$^{-1}$). The affinities of the two hek-L proteins for hek/Fc were equivalent and relatively high.

b) Elk Binding

The binding assay described above was repeated, substituting a soluble rat elk/Fc fusion protein for the hek/Fc fusion protein. Nucleotide and encoded amino acid sequences for rat elk are presented in Lhotak et al. (*Mol. Cell. Biol.* 11:2496, 1991). The elk/Fc fusion protein comprised the extracellular domain of elk fused to a native Fc region polypeptide derived from a human Ig 1 antibody. The indirect assay (using unlabeled elk/Fc and radioiodinated mouse anti-human IgG antibody) was employed because direct radiolabeling of elk/Fc inactivated the binding specificity thereof.

The results of the study were as follows:

TABLE II

| | Binding affinity for elk/Fc ($K_a$) |
|---|---|
| B61 | $23 \times 10^8$ M$^{-1}$; $7.0 \times 10^7$ M$^{-1}$ |
| elk-L | $1.08 \times 10^9$ M$^{-1}$ |
| hek-L A2 | $2.7 \times 10^8$ M$^{-1}$; $3.5 \times 10^7$ M$^{-1}$ |
| hek-L C6 | $1.3 \times 10^8$ M$^{-1}$; $5.4 \times 10^7$ M$^{-1}$ |

A biphasic pattern of elk/Fc binding was observed for B61 with Kas of $2.3 \times 10^8$ M$^{-1}$ and $7.0 \times 10^7$ M$^{-1}$. The affinity constant ($K_a$) shown for elk/Fc binding to transfected cells expressing elk-L matches well with those observed for binding of elk/Fc to the native ligand expressed on various rat neural cell lines. A biphasic pattern of elk/Fc binding is seen for both hek ligands.

EXAMPLE 6

Homology

The homology of the full length human elk-L, B61, hek ligand A2, and hek ligand C6 proteins (described in Example 5) for one another at the amino acid level are presented in Table III:

TABLE III

| | | % amino acid identity | | | |
|---|---|---|---|---|---|
| | | elk-L | B61 | A2 | C6 |
| % amino acid similarity | elk-L | | 33 | 28 | 32 |
| | B61 | 51 | | 40 | 37 |
| | A2 | 48 | 63 | | 38 |
| | C6 | 50 | 55 | 57 | |

The percent identity of the DNA sequences are presented in Table IV:

TABLE IV

| | % DNA identity | | | |
|---|---|---|---|---|
| | elk-L | B61 | A2 | C6 |
| elk-L | | 44.0 | 40.7 | 43.7 |
| B61 | | | 48.9 | 51.5 |
| A2 | | | | 47.3 |
| C6 | | | | |

---

What is claimed is:

1. An isolated nucleic acid encoding a hek-L protein capable of binding hek, wherein said nucleic acid comprises a nucleotide sequence that is at least 90% identical to at least one sequence selected from nucleotides 83–796, nucleotides 83–745, nucleotides 140–796, and nucleotides 140–745, of SEQ ID NO: 1.

2. An expression vector comprising a nucleic acid according to claim 1.

3. A process for preparing a hek-L polypeptide, comprising culturing a host cell transformed with a vector according to claim 2 under conditions promoting expression of hek-L, and recovering the hek-L polypeptide from the culture.

4. An isolated nucleic acid encoding a hek-L protein capable of binding hek, wherein said nucleic acid comprises a nucleotide sequence that is at least 90% identical to at least one sequence selected from nucleotides 28–630, nucleotides 28–573, nucleotides 94–630, and nucleotides 94–573, of SEQ ID NO: 3.

5. An expression vector comprising a nucleic acid according to claim 4.

6. A process for preparing a hek-L polypeptide, comprising culturing a host cell transformed with a vector according to claim 5 under conditions promoting expression of hek-L, and recovering the hek-L polypeptide from the culture.

7. An isolated nucleic acid encoding a human hek-L protein capable of binding hek, wherein said hek-L comprises an amino acid sequence that is at least 90% identical to at least one sequence selected from amino acids 1–202 of SEQ ID NO: 2 and amino acids 1–219 of SEQ ID NO: 2 and amino acids 1–160 of SEQ ID NO: 4 and amino acids 1–179 of SEQ ID NO: 4.

8. An expression vector comprising a nucleic acid according to claim 7.

9. A process for preparing a hek-L polypeptide, comprising culturing a host cell transformed with a vector according to claim 8 under conditions promoting expression of hek-L, and recovering the hek-L polypeptide from the culture.

10. An isolated nucleic acid encoding a fusion protein comprising a hek-L polypeptide that binds hek, and an Fc polypeptide, wherein said hek-L comprises an amino acid sequence that is at least 90% identical to at least one sequence selected from amino acids 1–202 of SEQ ID NO: 2 and amino acids 1–219 of SEQ ID NO: 2 and amino acids 1–160 of SEQ ID NO: 4 and amino acids 1–179 of SEQ ID NO: 4.

11. An expression vector comprising a nucleic acid according to claim 10.

12. A process for preparing a hek-L polypeptide, comprising culturing a host cell transformed with a vector according to claim 11 under conditions promoting expression of hek-L, and recovering the hek-L polypeptide from the culture.

* * * * *

UNITED STATES PATENT AND TRADEMARK OFFICE
CERTIFICATE OF CORRECTION

PATENT NO. : 6,949,366 B2
APPLICATION NO. : 09/904954
DATED : March 7, 2006
INVENTOR(S) : M. Patricia Beckmann et al.

It is certified that error appears in the above-identified patent and that said Letters Patent is hereby corrected as shown below:

Title page,
Item [73], Assignee, "Amgen Inc., Thousand Oaks, CA (US)" should read
-- Immunex Corporation, Seattle, WA (US) --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,949,366 B2 | Page 1 of 1 |
| APPLICATION NO. | : 09/904954 | |
| DATED | : September 27, 2005 | |
| INVENTOR(S) | : M. Patricia Beckmann et al. | |

It is certified that error appears in the above-identified patent and that said Letters Patent is hereby corrected as shown below:

Title page,
Item [73], Assignee, "Amgen Inc., Thousand Oaks, CA (US)" should read
-- Immunex Corporation, Seattle, WA (US) --.

This certificate supersedes certificate of correction issued June 27, 2006.

Signed and Sealed this

Twenty-ninth Day of August, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,949,366 B2 | Page 1 of 1 |
| APPLICATION NO. | : 09/904954 | |
| DATED | : September 27, 2005 | |
| INVENTOR(S) | : M. Patricia Beckmann and Douglas P. Cerretti | |

It is certified that error appears in the above-identified patent and that said Letters Patent is hereby corrected as shown below:

On the title page, item (54), the title, and Column 1, lines 1 and 2, "CYTOKINES THAT BIND THE CELL SURFACE RECEPTOR HEK" should read -- DNA ENCODING A HEK-LIGAND POLYPEPTIDE --.

Signed and Sealed this

Twenty-fourth Day of July, 2007

JON W. DUDAS
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1037 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
      (B) CLONE: hek-L A2

(ix) FEATURE:
      (A) NAME/KEY: CDS
      (B) LOCATION: 83..799

(ix) FEATURE:
      (A) NAME/KEY: sig_peptide
      (B) LOCATION: 83..139

(ix) FEATURE:
      (A) NAME/KEY: mat_peptide
      (B) LOCATION: 140..796

(xi) SEQUENCE DESCRIPTION: SEQ ID NO: 1:

```
GGATCTTGGA ACGAGACGAC CTGCTGGAGA AGCCGGGAGC GCGGGGCTCA GTCGGGGGGC         60

GGCGGCGGCG GCGGCTCCGG GG ATG GCG GCG GCT CCG CTG CTG CTG CTG CTG        112
                         Met Ala Ala Ala Pro Leu Leu Leu Leu Leu
                         -19             -15                 -10
```

```
CTG CTC GTG CCC GTG CCG CTG CTG CCG CTG CTG GCC CAA GGG CCC GGA      160
Leu Leu Val Pro Val Pro Leu Leu Pro Leu Leu Ala Gln Gly Pro Gly
             -5                   1                   5

GGG GCG CTG GGA AAC CGG CAT GCG GTG TAC TGG AAC AGC TCC AAC CAG      208
Gly Ala Leu Gly Asn Arg His Ala Val Tyr Trp Asn Ser Ser Asn Gln
         10                  15                  20

CAC CTG CGG CGA GAG GGC TAC ACC GTG CAG GTG AAC GTG AAC GAC TAT      256
His Leu Arg Arg Glu Gly Tyr Thr Val Gln Val Asn Val Asn Asp Tyr
     25                  30                  35

CTG GAT ATT TAC TGC CCG CAC TAC AAC AGC TCG GGG GTG GGC CCC GGG      304
Leu Asp Ile Tyr Cys Pro His Tyr Asn Ser Ser Gly Val Gly Pro Gly
 40                  45                  50                  55

GCG GGA CCG GGG CCC GGA GGC GGG GCA GAG CAG TAC GTG CTG TAC ATG      352
Ala Gly Pro Gly Pro Gly Gly Gly Ala Glu Gln Tyr Val Leu Tyr Met
                 60                  65                  70

GTG AGC CGC AAC GGC TAC CGC ACC TGC AAC GCC AGC CAG GGC TTC AAG      400
Val Ser Arg Asn Gly Tyr Arg Thr Cys Asn Ala Ser Gln Gly Phe Lys
             75                  80                  85

CGC TGG GAG TGC AAC CGG CCG CAC GCC CCG CAC AGC CCC ATC AAG TTC      448
Arg Trp Glu Cys Asn Arg Pro His Ala Pro His Ser Pro Ile Lys Phe
         90                  95                 100

TCG GAG AAG TTC CAG CGC TAC AGC GCC TTC TCT CTG GGC TAC GAG TTC      496
Ser Glu Lys Phe Gln Arg Tyr Ser Ala Phe Ser Leu Gly Tyr Glu Phe
    105                 110                 115

CAC GCC GGC CAC GAG TAC TAC TAC ATC TCC ACG CCC ACT CAC AAC CTG      544
His Ala Gly His Glu Tyr Tyr Tyr Ile Ser Thr Pro Thr His Asn Leu
120                 125                 130                 135

CAC TGG AAG TGT CTG AGG ATG AAG GTG TTC GTC TGC TGC GCC TCC ACA      592
His Trp Lys Cys Leu Arg Met Lys Val Phe Val Cys Cys Ala Ser Thr
                140                 145                 150

TCG CAC TCC GGG GAG AAG CCG GTC CCC ACT CTC CCC CAG TTC ACC ATG      640
Ser His Ser Gly Glu Lys Pro Val Pro Thr Leu Pro Gln Phe Thr Met
            155                 160                 165

GGC CCC AAT GTG AAG ATC AAC GTG CTG GAA GAC TTT GAG GGA GAG AAC      688
Gly Pro Asn Val Lys Ile Asn Val Leu Glu Asp Phe Glu Gly Glu Asn
        170                 175                 180

CCT CAG GTG CCC AAG CTT GAG AAG AGC ATC AGC GGG ACC AGC CCC AAA      736
Pro Gln Val Pro Lys Leu Glu Lys Ser Ile Ser Gly Thr Ser Pro Lys
    185                 190                 195

CGG GAA CAC CTG CCC CTG GCC GTG GGC ATC GCC TTC TTC CTC ATG ACG      784
Arg Glu His Leu Pro Leu Ala Val Gly Ile Ala Phe Phe Leu Met Thr
200                 205                 210                 215

TTC TTG GCC TCC TAGCTCTGCC CCCTCCCCTG GGGGGGAGA GATGGGGCGG           836
Phe Leu Ala Ser
            220

GGCTTGGAAG GAGCAGGGAG CCTTTGGCCT CTCCAAGGGA AGCCTAGTGG GCCTAGACCC    896

CTCCTCCCAT GGCTAGAAGT GGGGCCTGCA CCATACATCT GTGTCCGCCC CCTCTACCCC    956

TTCCCCCCAC GTAGGGCACT GTAGTGGACC AAGCACGGGG ACAGCCATGG GTCCCGAGCA   1016

GGTCGTCTCG TTCCAAGATC C                                             1037
```

(2) INFORMATION FOR SEQ ID NO: 2:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Ala Ala Pro Leu Leu Leu Leu Leu Val Pro Val Pro
-19          -15              -10              -5

Leu Leu Pro Leu Leu Ala Gln Gly Pro Gly Gly Ala Leu Gly Asn Arg
         1               5                    10

His Ala Val Tyr Trp Asn Ser Ser Asn Gln His Leu Arg Arg Glu Gly
     15              20              25

Tyr Thr Val Gln Val Asn Val Asn Asp Tyr Leu Asp Ile Tyr Cys Pro
 30              35              40              45

His Tyr Asn Ser Ser Gly Val Gly Pro Gly Ala Gly Pro Gly Pro Gly
             50              55              60

Gly Gly Ala Glu Gln Tyr Val Leu Tyr Met Val Ser Arg Asn Gly Tyr
             65              70              75

Arg Thr Cys Asn Ala Ser Gln Gly Phe Lys Arg Trp Glu Cys Asn Arg
         80              85              90

Pro His Ala Pro His Ser Pro Ile Lys Phe Ser Glu Lys Phe Gln Arg
         95              100             105

Tyr Ser Ala Phe Ser Leu Gly Tyr Glu Phe His Ala Gly His Glu Tyr
110             115             120             125

Tyr Tyr Ile Ser Thr Pro Thr His Asn Leu His Trp Lys Cys Leu Arg
             130             135             140

Met Lys Val Phe Val Cys Cys Ala Ser Thr Ser His Ser Gly Glu Lys
             145             150             155

Pro Val Pro Thr Leu Pro Gln Phe Thr Met Gly Pro Asn Val Lys Ile
             160             165             170

Asn Val Leu Glu Asp Phe Glu Gly Glu Asn Pro Gln Val Pro Lys Leu
175             180             185

Glu Lys Ser Ile Ser Gly Thr Ser Pro Lys Arg Glu His Leu Pro Leu
190             195             200             205

Ala Val Gly Ile Ala Phe Phe Leu Met Thr Phe Leu Ala Ser
             210             215
```

(2) INFORMATION FOR SEQ ID NO: 3:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
        (B) CLONE: hek-L C6

(ix) FEATURE:
        (A) NAME/KEY: mat_peptide
        (B) LOCATION: 94..630

(ix) FEATURE:
        (A) NAME/KEY: CDS
        (B) LOCATION: 28..633

(ix) FEATURE:
        (A) NAME/KEY: sig_peptide
        (B) LOCATION: 28..93

(xi) SEQUENCE DESCRIPTION: SEQ ID NO: 3:

```
GCCAGACCAA ACCGGACCTC GGGGGCG ATG CGG CTG CTG CCC CTG CTG CGG         51
                              Met Arg Leu Leu Pro Leu Leu Arg
                              -22     -20             -15

ACT GTC CTC TGG GCC GCG TTC CTC GGC TCC CCT CTG CGC GGG GGC TCC        99
Thr Val Leu Trp Ala Ala Phe Leu Gly Ser Pro Leu Arg Gly Gly Ser
            -10                 -5                          1

AGC CTC CGC CAC GTA GTC TAC TGG AAC TCC AGT AAC CCC AGG TTG CTT       147
Ser Leu Arg His Val Val Tyr Trp Asn Ser Ser Asn Pro Arg Leu Leu
        5                10                  15

CGA GGA GAC GCC GTG GTG GAG CTG GGC CTC AAC GAT TAC CTA GAC ATT       195
Arg Gly Asp Ala Val Val Glu Leu Gly Leu Asn Asp Tyr Leu Asp Ile
    20                  25                  30

GTC TGC CCC CAC TAC GAA GGC CCA GGG CCC CCT GAG GGC CCC GAG ACG       243
Val Cys Pro His Tyr Glu Gly Pro Gly Pro Pro Glu Gly Pro Glu Thr
35              40                  45                      50

TTT GCT TTG TAC ATG GTG GAC TGG CCA GGC TAT GAG TCC TGC CAG GCA       291
Phe Ala Leu Tyr Met Val Asp Trp Pro Gly Tyr Glu Ser Cys Gln Ala
                55                  60                  65

GAG GGC CCC CGG GCC TAC AAG CGC TGG GTG TGC TCC CTG CCC TTT GGC       339
Glu Gly Pro Arg Ala Tyr Lys Arg Trp Val Cys Ser Leu Pro Phe Gly
            70                  75                  80

CAT GTT CAA TTC TCA GAG AAG ATT CAG CGC TTC ACA CCT TTC TCC CTC       387
His Val Gln Phe Ser Glu Lys Ile Gln Arg Phe Thr Pro Phe Ser Leu
        85                  90                  95

GGC TTT GAG TTC TTA CCT GGA GAG ACT TAC TAC TAC ATC TCG GTG CCC       435
Gly Phe Glu Phe Leu Pro Gly Glu Thr Tyr Tyr Tyr Ile Ser Val Pro
    100                 105                 110

ACT CCA GAG AGT TCT GGC CAG TGC TTG AGG CTC CAG GTG TCT GTC TGC       483
Thr Pro Glu Ser Ser Gly Gln Cys Leu Arg Leu Gln Val Ser Val Cys
115                 120                 125                 130

TGC AAG GAG AGG AAG TCT GAG TCA GCC CAT CCT GTT GGG AGC CCT GGA       531
Cys Lys Glu Arg Lys Ser Glu Ser Ala His Pro Val Gly Ser Pro Gly
                135                 140                 145

GAG AGT GGC ACA TCA GGG TGG CGA GGG GGG GAC ACT CCC AGC CCC CTC       579
Glu Ser Gly Thr Ser Gly Trp Arg Gly Gly Asp Thr Pro Ser Pro Leu
            150                 155                 160

TGT CTC TTG CTA TTA CTG CTG CTT CTG ATT CTT CGT CTT CTG CGA ATT       627
Cys Leu Leu Leu Leu Leu Leu Leu Ile Leu Arg Leu Leu Arg Ile
        165                 170                 175

CTG TGAGCC                                                            636
Leu
    180

(2) INFORMATION FOR SEQ ID NO: 4:

(i) SEQUENCE CHARACTERISTICS:
        (A) LENGTH: 201 amino acids
        (B) TYPE: amino acid
        (D) TOPOLOGY: linear (ii) MOLECULE TYPE: protein (xi) SEQUENCE DESCRIPTION: SEQ ID NO: 4:

Met Arg Leu Leu Pro Leu Leu Arg Thr Val Leu Trp Ala Ala Phe Leu
-22     -20             -15                 -10

Gly Ser Pro Leu Arg Gly Gly Ser Ser Leu Arg His Val Val Tyr Trp
    -5                  1               5                   10

Asn Ser Ser Asn Pro Arg Leu Leu Arg Gly Asp Ala Val Val Glu Leu
                15                  20                  25

Gly Leu Asn Asp Tyr Leu Asp Ile Val Cys Pro His Tyr Glu Gly Pro
            30                  35                  40
```

```
Gly Pro Pro Glu Gly Pro Glu Thr Phe Ala Leu Tyr Met Val Asp Trp
         45              50                  55

Pro Gly Tyr Glu Ser Cys Gln Ala Glu Gly Pro Arg Ala Tyr Lys Arg
         60              65              70

Trp Val Cys Ser Leu Pro Phe Gly His Val Gln Phe Ser Glu Lys Ile
 75              80              85                          90

Gln Arg Phe Thr Pro Phe Ser Leu Gly Phe Glu Phe Leu Pro Gly Glu
             95             100             105

Thr Tyr Tyr Tyr Ile Ser Val Pro Thr Pro Glu Ser Ser Gly Gln Cys
             110            115             120

Leu Arg Leu Gln Val Ser Val Cys Cys Lys Glu Arg Lys Ser Glu Ser
         125             130             135

Ala His Pro Val Gly Ser Pro Gly Glu Ser Gly Thr Ser Gly Trp Arg
         140             145             150

Gly Gly Asp Thr Pro Ser Pro Leu Cys Leu Leu Leu Leu Leu Leu Leu
155             160             165             170

Leu Ile Leu Arg Leu Leu Arg Ile Leu
             175
```